United States Patent
Eversmann et al.

(10) Patent No.: US 7,809,432 B2
(45) Date of Patent: Oct. 5, 2010

(54) EVENT DETECTION—APPARATUS AND METHOD FOR MEASURING THE ACTIVITY OF NEURAL NETWORKS

(75) Inventors: Bjorn-Oliver Eversmann, Munich (DE); Martin Jenkner, Planegg (DE); Christian Paulus, Weilheim (DE); Roland Thewes, Grobenzell (DE)

(73) Assignee: Infineon Technologies AG, Neubiberg (DE)

( * ) Notice: Subject to any disclaimer, the term of this patent is extended or adjusted under 35 U.S.C. 154(b) by 1749 days.

(21) Appl. No.: 10/964,560

(22) Filed: Oct. 12, 2004

(65) Prior Publication Data

US 2005/0107893 A1    May 19, 2005

Related U.S. Application Data

(63) Continuation of application No. PCT/EP03/03355, filed on Mar. 31, 2003.

(30) Foreign Application Priority Data

Apr. 12, 2002   (DE)   ................ 102 16 243

(51) Int. Cl.
*A61B 5/00*   (2006.01)
(52) U.S. Cl. ..................................... 600/544
(58) Field of Classification Search .............. None
See application file for complete search history.

(56) References Cited

U.S. PATENT DOCUMENTS 3,978,847 A * 9/1976 Fehmi et al. ................ 600/545
4,969,468 A * 11/1990 Byers et al. ................. 600/373
5,349,962 A * 9/1994 Lockard et al. ............. 600/545
6,171,239 B1 * 1/2001 Humphrey ................... 600/372
2002/0103512 A1 * 8/2002 Echauz et al. .................. 607/9
2004/0082875 A1 * 4/2004 Donoghue et al. .......... 600/544

FOREIGN PATENT DOCUMENTS

WO    WO-00/14521 A1    3/2000

OTHER PUBLICATIONS

Kim, C. et al.: "A 64-Site Multishank CMOS Low-Profile Neural Stimulating Probe"; Sep. 9, 1996; IEEE Journal of Solid-State Circuits; IEEE Inc., New York, NY US; pp. 1230-1238, vol. 31.

(Continued)

*Primary Examiner*—Robert L Nasser
(74) *Attorney, Agent, or Firm*—Dickstein Shapiro LLP

(57) ABSTRACT

Apparatus for measuring neural network activity with a textured semiconductor substrate. Sensor elements have a respective detection electrode on the substrate surface for detecting neural network signals, and the detected neural signals are a basis for outputting electrical sensor output signals via respective sensor element outputs. Each amplifier element has an input and an output. Each of the sensor elements has associated therewith one of the amplifier elements whose input is connected to the sensor output of the respective sensor element. The amplified sensor output signal is output the amplifier output as an amplifier output signal. An activity evaluator has an input, which is connected to at least one of the amplifier outputs, and an output. The activity evaluation device produces an activity signal, which is a measure of activity of the neural network, based on the amplifier output signal, and outputs the amplifier output signal via the evaluation output.

15 Claims, 15 Drawing Sheets

OTHER PUBLICATIONS

Rambo, K.J. et al.: "VLSI silicon based prosthesis for in vitro measurement of neural activity"; Proceedings of the Custom Integrated Circuits Conference, San Diego, May 12-15, 1991, New York, IEEE, US, vol. CONF. 13, May 12, 1991; pp. 27.7.1-27.7.4.

Oka, H. et al.: "A new planar multielectrode array for extracellular recording: application to hippocampal acute slice"; Journal of Neuroscience Methods 93 (1999) pp. 61-67; 1999 Elsevier Science B.V.

* cited by examiner

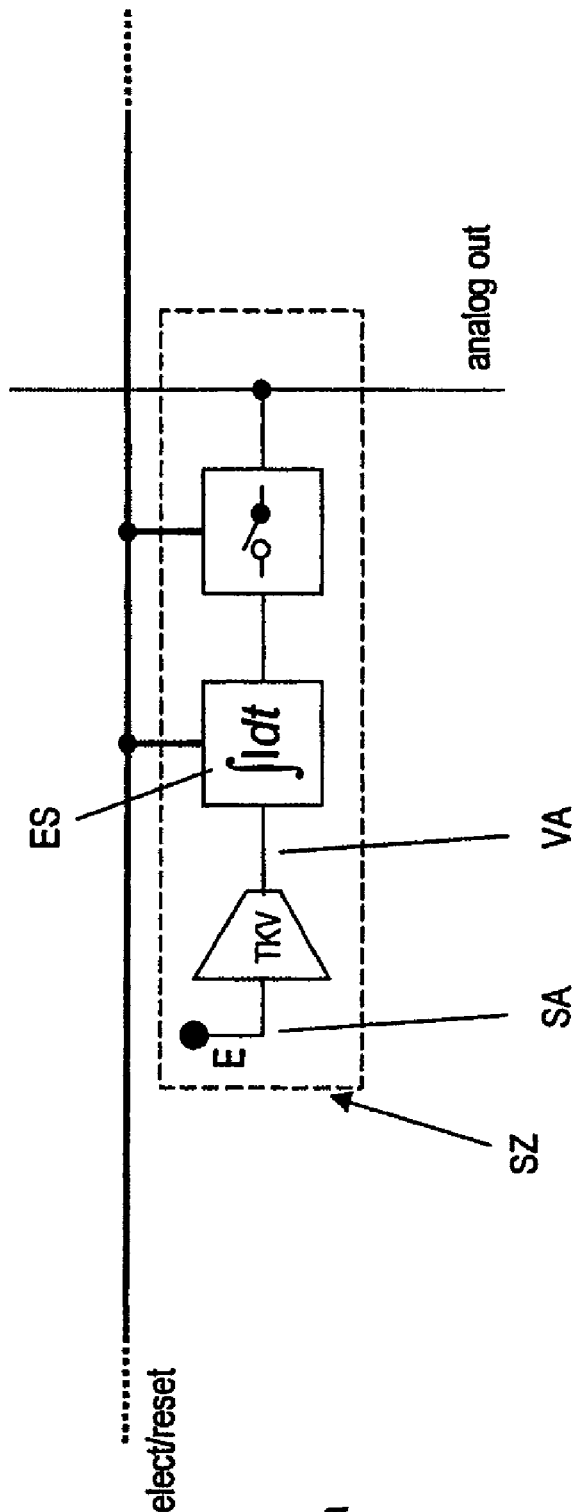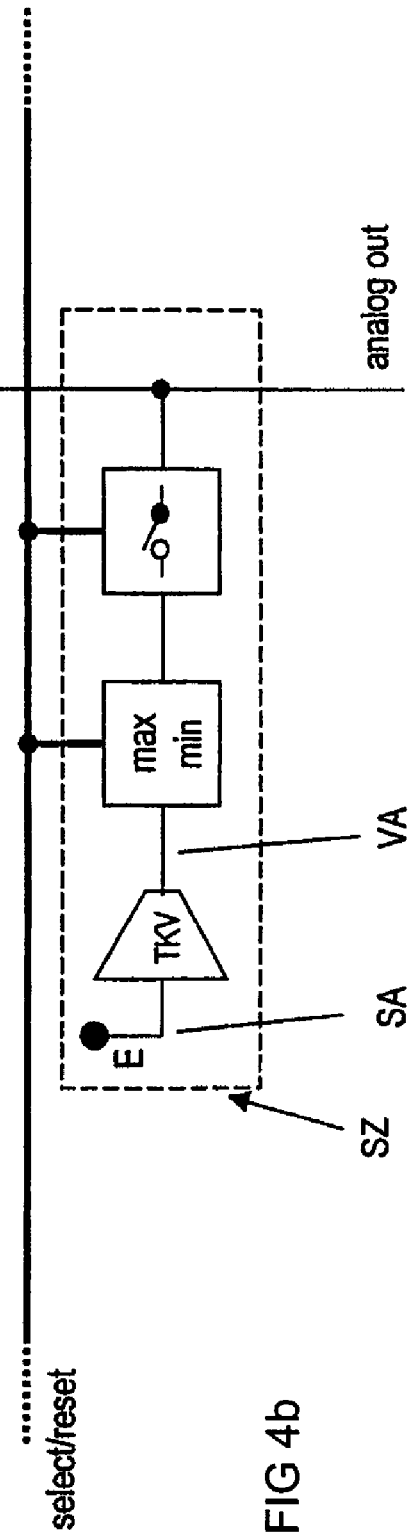

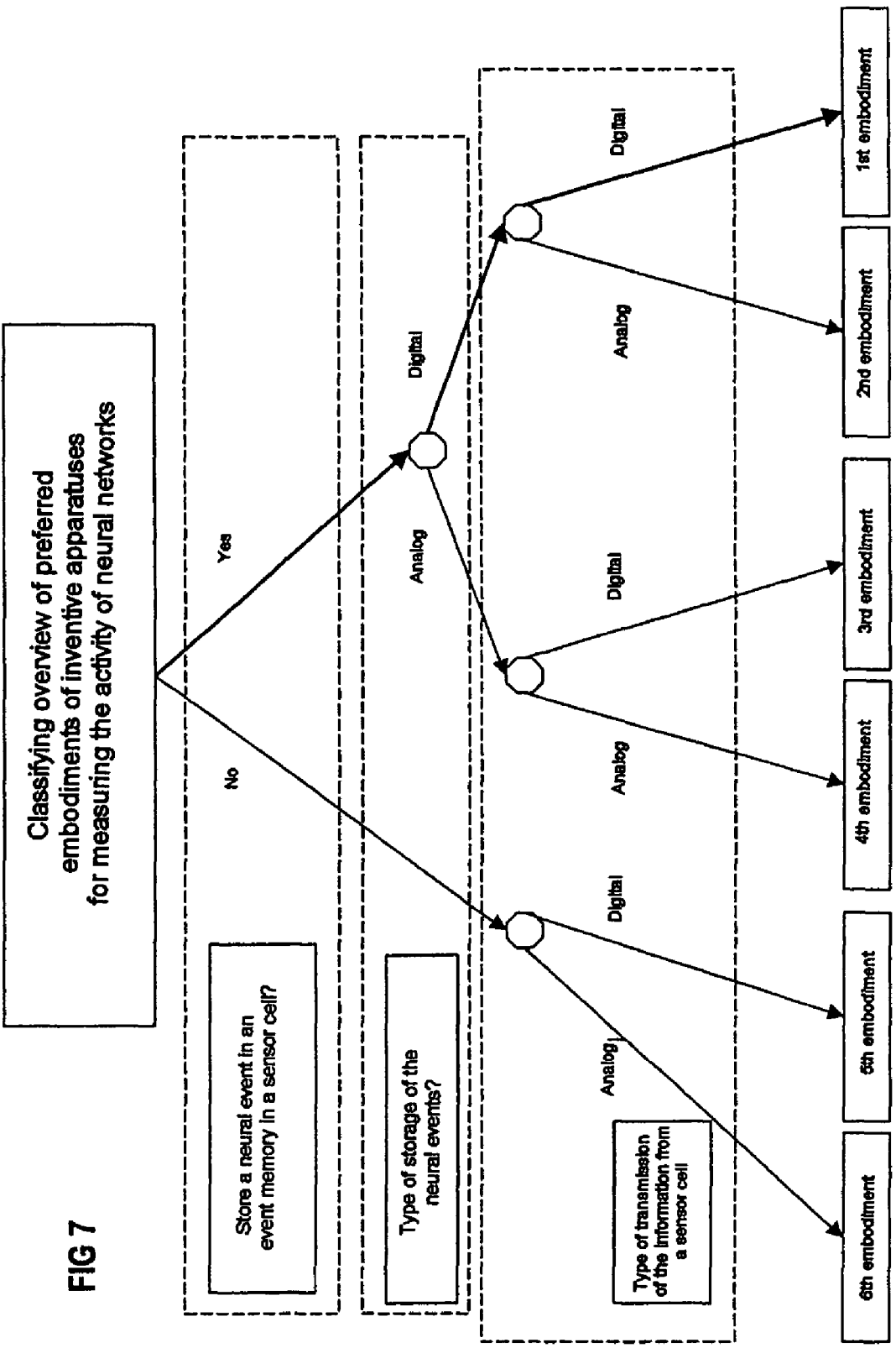

EVENT DETECTION—APPARATUS AND METHOD FOR MEASURING THE ACTIVITY OF NEURAL NETWORKS

CROSS-REFERENCE TO RELATED APPLICATION

This application is a continuation of International Patent Application Ser. No. PCT/EP03/03355, filed Mar. 31, 2003, which published in German on Oct. 23, 2003 as WO 2003/088141, and is incorporated herein by reference in its entirety.

FIELD OF THE INVENTION

The invention relates to an apparatus for measuring the activity of neural networks, and to a method for measuring the activity of neural network.

BACKGROUND OF THE INVENTION

The main area of application for an apparatus or method based on the invention is, in particular, sensitive and rapid analysis of chemical substances and, in particular, rapid and reliable assessment of the toxicity of unknown substances.

Previous methods of analysis of the toxicity of chemical substances are usually based on classical, typically wet-chemical, analyses and on spectroscopic and physicochemical measurement methods. Such methods of analysis usually have a comparatively complex apparatus design, require long analysis times and/or often have unsatisfactory detection sensitivity. In the case of conventional methods of analysis, the detection threshold for the substance or mixture of substances to be analyzed is often comparatively high, in particular.

In first approaches, the prior art also uses neural networks for analyzing particularly the toxicity of chemical substances. In this context, the neural activity of the neural network is usually detected using the technique of "patch clamping" or extracellular microelectrodes. Patch clamping involves invasive, intracellular signal derivation, while extracellular microelectrodes use a noninvasive method of detection with extracellular signal derivation. In both cases, an external measuring amplifier is connected to the detection electrodes and accords the time profile of the corresponding electrical voltage. The external measuring amplifier thus delivers voltage/time signal profiles—"transients"—for neural signals, which are subsequently evaluated.

To increase the yield of suitable nerve cells with which correct contact has been made and also the statistical meaningfulness, the use of regularly arranged sensors is known. In this context, reference is made particularly to the publication by Oka et al. "A new planar multielectrode array for extracellular recording: Application to hippocampal acute slice" in Journal of Neuroscience Methods 93 (1999), pages 61-67, Elsevier.

Although such sensor arrangements allow resolved-time signal detection of individual neurons on the sensor, they have only limited use for reliably and rapidly assessing particularly the toxicity of unknown substances.

SUMMARY OF THE INVENTION

Accordingly, it is an object of the invention to specify an apparatus and a method which can be used for rapidly and reliably assessing particularly the toxicity of substances or mixtures of substances.

This object is achieved by an apparatus for measuring the activity of neural networks and by a method for measuring the activity of neural networks.

In line with the invention, an apparatus for measuring the activity of neural networks comprises a textured semiconductor substrate comprising a multiplicity of sensor elements with at least one respective electrically conductive detection electrode which is arranged on the surface of the semiconductor substrate for detecting neural signals from a neural network, the sensor elements being designed such that the detected neural signals can be taken as a basis for outputting electrical sensor output signals via respective sensor outputs on the sensor elements;

a multiplicity of amplifier elements with at least one respective amplifier input and at least one respective amplifier output, each of the sensor elements having associated one of the amplifier elements whose amplifier input is electrically connected to the sensor output of the respective sensor element, and the amplified sensor output signal being able to be output as an amplifier output signal via the amplifier output; and at least one activity evaluation device with at least one evaluation input and at least one evaluation output, the evaluation input being electrically connected to at least one of the amplifier outputs, and the activity evaluation device being designed to produce an activity signal, which is a measure of the activity of the neural network, on the basis of the amplifier output signal and to output it via the evaluation output.

The inventive apparatus for measuring or determining the activity of neural networks is thus a sensor structure which is monolithically integrated in a semiconductor substrate and delivers an activity signal which is a direct measure of the activity of the neural network which is to be examined. To this end, the apparatus comprises a multiplicity of sensor elements or signal pickups which are designed for detecting a neural signal from a neuron. Each of these sensor elements has a directly associated amplifier element which amplifies the sensor output signal from the sensor element, which is normally a voltage signal. The sensor output signal amplified in this manner, which is called the amplifier output signal, can be read by the activity evaluation device. In this context, the activity evaluation device is designed such that it can take the amplifier output signal as a basis for producing an activity signal which is a measure of the activity of the neural network.

The invention makes use of the knowledge that all rapidly acting toxic substances or mixtures of substances, such as those used in drugs or biological or chemical warfare agents, act on the nerve system. The action of such substances or mixtures of substances can be seen particularly from the alteration in the electrical activity in the neural network. In this context, one crucial parameter of this electrical activity in the neural network is the frequency at which the nerve cells generate electrical pulses. The generation of an electrical pulse by a nerve cell, which is also referred to as "firing" of the nerve cell, is manifested particularly in a temporary conductivity increase for potassium and sodium currents between the cell interior and the cell exterior. This results in an abrupt change in the electrical potential in the gap between the detection electrode E and the supported arrangement of neural cells. This arrangement may range from an individual neural cell (single unit) through accumulations of a plurality of neural cells to highly dense layers of neural tissue (multi-unit). The frequency spectrum for such signals typically has a bandwidth of up to 5 kHz, the amplitude of the neural signal which can be detected at the detection electrode E being in the order of magnitude of 1 mV. If neurotoxic substances are applied, then, inter alia, the pulse frequency of the nerve cells alters. Such an alteration in the pulse frequency or in the correlation of the pulses from the nerve cells can actually be used to infer the quantity and the type of the neuroactive substance.

Besides applications in pharmacology and in environmental monitoring, there is a great deal of interest in such universally useable sensor arrangements particularly in the field of safety engineering and military areas of application. By way of example, sensor arrangements which permit a user to examine unknown gases or liquids quickly and reliably for their toxic action would have diverse opportunities for use.

In this context, the inventive apparatus effectively overcomes the problems which arise in the above-described conventional sensor arrangements (particularly microelectrode arrays) when determining the activity of neural networks. As set out in the introduction, conventional sensor arrangements involve the transfer of voltage/time signal profiles for neural events, "transients" from the sensor arrangement to an external amplifier for amplification and further evaluation. To be able to obtain a reliable and statistically relevant evaluation of the activity of the neural network, however, a large number of such transients need to be transferred and evaluated. This results in an "imaging problem", where transfer bottlenecks arise when transferring the extensive transient data to the external measurement amplifier or to an external evaluation computer.

Since the voltage signal generated by a neuron during "firing" is typically characterized by a frequency spectrum with a bandwidth of 5 kHz, it is necessary to record transients at sampling rates of at least 10 kHz. If, by way of example, a microelectrode arrangement containing $100 \times 100 = 10^4$ electrodes needs to be recorded at a resolution of 8 bits, then just a sampling rate of 10 kHz results in a data volume of approximately 800 megabits/second which need to be transferred to the external measurement amplifier or to an external computer. This requires a very complex broadband bus architecture, which significantly complicates and increases the cost of the sensor arrangement.

The invention solves this problem preferably by means of data reduction using "event characterization" in the apparatus itself. In line with the invention, the transient data are not transferred, i.e. the voltage/time signal profiles for neural signals are not transferred from the sensor elements to the activity evaluation device. Instead, event assessment or characterization takes place actually in the sensor cells, the result being that event information is produced which is substantially compressed as compared with the transient data. This means that the inventive apparatus is used for detecting the (overall) activity of a neural network and not for direct continuous-time signal tracking of transients which are detected on individual sensor elements.

As compared with multielectrode arrays (MEAs) which are available commercially today, the invention permits a further significant increase in the density of detection electrodes on the sensor surface to be produced by utilizing the production methods known from microelectronics.

For signal derivation for the neural signal, there is a detection electrode on or close to the surface of the semiconductor substrate which taps off the neural signal on a capacitive/resistive basis. If there is provision for purely capacitive coupling to the neurons, then the detection electrode may be coated with a dielectric. Preferably, the detection electrode has an electrode area which is approximately the same size as or is smaller than the typical bearing area for a neuron on the sensor surface. When rat neurons are used, this gives a preferred electrode diameter of approximately 10 μm, for example.

When a neuron in the neural network fires, this signifies a temporary conductivity increase for potassium and sodium currents between the cell interior and the cell exterior. This results in an abrupt change in the potential in the gap between the detection electrode and the supported arrangement of neural cells. This arrangement can range from an individual neural cell (single unit) through accumulations of a plurality of neural cells to highly dense layers of neural tissue (multiunit). The frequency spectrum for such signals typically has a bandwidth of up to 5 kHz, the amplitude of the signal which can be detected at the detection electrode being in the order of magnitude of 1 millivolt.

Preferably, the amplifier element, which is connected to the output of the sensor element, amplifies this neural signal by several orders of magnitude and/or converts it into an output current.

In line with one preferred embodiment of the invention, a multiplicity of sensor cells is provided which respectively comprise one of the sensor elements with its associated amplifier element. Preferably, the sensor cells are arranged in matrix form, particularly in orthogonal matrix form, in order to form a sensor cell array or a matrix. Each sensor element thus has a directly associated amplifier element which is located in the same sensor cell, i.e. in the direct physical surroundings of the sensor element. By way of example, at least regions of the amplifier element are below the detection electrode in the normal direction of the semiconductor substrate, which means that a highly integratable sensor cell design is obtained. The matrix-like arrangement of such sensor cells to form a sensor cell array has similarities with the arrangement structures which are known from DRAMs.

In line with one preferred embodiment, the activity evaluation device has a multiplicity of event memories for storing neural events and also at least one memory reading device for reading the event memories. Preferably, the activity evaluation device also has a control device which can be used to reset the event memories or to trigger a "reset".

Preferably, each of the sensor cells comprises one of the event memories, whose event memory input is connected to the amplifier output. In this context, the electrical connection between amplifier output and event memory input can—as also in the case of other electrical signal connections within the context of this invention—be conveyed by interposed components. Accordingly, in the case of this embodiment, the neural events or event information is/are stored or bufferstored in each sensor cell in the sensor cell array. In addition, there may also be provision for further storage of the neural events outside the sensor cells.

Preferably, each of the event memories can be selected by means of a select line in the activity evaluation device for selective reading by the memory reading device. The reading operation for the event memories takes place, by way of example, in a similar manner to that in the case of DRAM memory elements. Following appropriate addressing of the sensor cell (or of the event memory in the sensor cell), the content of the event memory can be requested on a column or evaluation line.

In line with one preferred embodiment, the activity evaluation device is designed for reading the event memories in predetermined time periods and for producing the activity signal on the basis of the memory contents read from the event memories per time period. If the event memory is a digital memory chip, then the memory content should preferably be understood to mean the number of neural events stored. Preferably, each neural event, which manifests itself in a complex voltage/time signal profile (for the transients), is represented merely by one binary information item. The transient data are thus subjected to data compression to produce binary data. If the event memory is an analog memory element, then the memory content may be the transient signal integrated over time, for example.

Preferably, the amplifier elements are connected to the associated event memories by means of respective threshold value detector elements for discretizing the amplifier output signals. The amplifier element in each sensor cell preferably has a threshold value detector element connected downstream of it which outputs a pulse signal or trigger signal when the threshold value of the threshold value detector element is exceeded by the amplifier output signal. Preferably, the threshold value of the threshold value detector element can be set externally by a "threshold" line using the activity evaluation device.

Preferably, the amplifier elements are connected to the associated threshold value detector elements via respective rectification elements for rectifying the amplifier output signal. Such rectification elements are advantageous, since the polarity of the neural signal contains no information which is necessary for assessing the activity of the neural network. It may therefore be expedient to rectify the amplifier output signal first.

In line with one preferred embodiment, the event memory elements are digital memory elements, particularly digital counters. In this context, the counters are advantageously designed such that the counter reading is incremented by a voltage pulse which is output by the threshold value detector element connected upstream, for example. The counter reading is thus a measure of the number of neural events in the query period.

In line with a further preferred embodiment, the event memory elements are analog memory elements, particularly analog integrators or analog minimum or maximum memories.

In line with a further preferred embodiment, the amplifier elements are transconductance amplifier elements for producing a current signal as amplifier output signal. In this context, the voltage signal which is applied to the amplifier input of the amplifier element is converted into a current signal which is output for further processing at the amplifier output.

In line with a further preferred embodiment, the amplifier elements are transconductance amplifier elements for producing a current signal as amplifier output signal. The amplifier outputs of at least two of the amplifier elements are preferably connected to the activity evaluation device by means of a single evaluation or output line, which means that the current signals from the two amplifier elements are added. The activity evaluation device is preferably designed such that the activity signal can be produced on the basis of the amplitude of the added current signal.

In line with this embodiment, each sensor cell thus contains a transconductance amplifier which amplifies the detected neural signal voltage and converts it—preferably linearly—into a current. These currents are added on common evaluation lines through parallel connection of the sensor cells to produce a summed current and are evaluated at the edge of the sensor cell array or matrix. The amplitude of this current which varies over time is a direct measure of the activity of the neural network and represents one possible activity signal.

Since this method does not involve any discretization of the neural events within the sensor cells, these cells may be of very simple design and may thus have a small area. Such a concept allows a high level of integration for memory cells, which means that a sensor cell array with a large scale of integration can be created. However, a drawback of this concept is that each connected sensor cell provides a noise contribution which adds up on the evaluation line and impairs the signal-to-noise ratio.

Preferably, the amplifier outputs of all amplifier elements are connected to the activity evaluation device by means of a single evaluation line.

Advantageously, the amplifier elements can be connected to the activity evaluation device by means of a single evaluation line via respective threshold value detector elements for discretizing the amplifier output signals and downstream reference current sources.

In line with a further particularly preferred embodiment, at least two of the sensor cells are connected to one another for signaling purposes such that at least one signal from the sensor cells can be interchanged between the sensor cells. This signal may be any analog or digital signal which occurs in the sensor cells, particularly the sensor output signal, the amplifier output signal or other signals described above. This means that the sensor cells can also interchange (event) information with one another directly. Preferably, the sensor cells in the direct vicinity interchange information of analog or digital type about neural events in order to permit a further improvement in the detection sensitivity and/or further miniaturization of the sensor cells and/or preprocessing of the recorded information.

In line with a further aspect of the invention, the invention proposes a method for measuring the activity of neural networks using an apparatus based on the invention as mentioned above, having the following steps:

the neural signals are detected using the multiplicity of sensor elements;

the sensor output signals are produced and output on the basis of the detected neural signals;

the sensor output signals are amplified using the respective amplifier elements in order to produce the amplifier output signals; and the activity signal, which is a measure of the activity of the neural network, is produced on the basis of the amplifier output signals.

BRIEF DESCRIPTION OF THE DRAWINGS

The invention is described in detail below with reference to accompanying drawings of preferred embodiments. It should be understood that individual features described merely in connection with one embodiment may also be used in other embodiments. In the figures:

FIGS. 4*a*, 4*b*, and 4*c* show schematic block diagrams of fourth embodiments of the invention;

FIG. 7 shows a classifying overview of preferred embodiments of inventive apparatuses for measuring the activity of neural networks;

DETAILED DESCRIPTION OF THE PREFERRED MODE OF THE INVENTION

FIG. 7 shows a classifying overview of the preferred embodiments which are to be described below for sensor cells in inventive apparatuses. In this context, the embodiments are classified into a total of six embodiments according to the manner of event storage and event information transfer. It should be understood that features which are described only in connection with one embodiment may also be used in connection with other embodiments.

Figure 1:
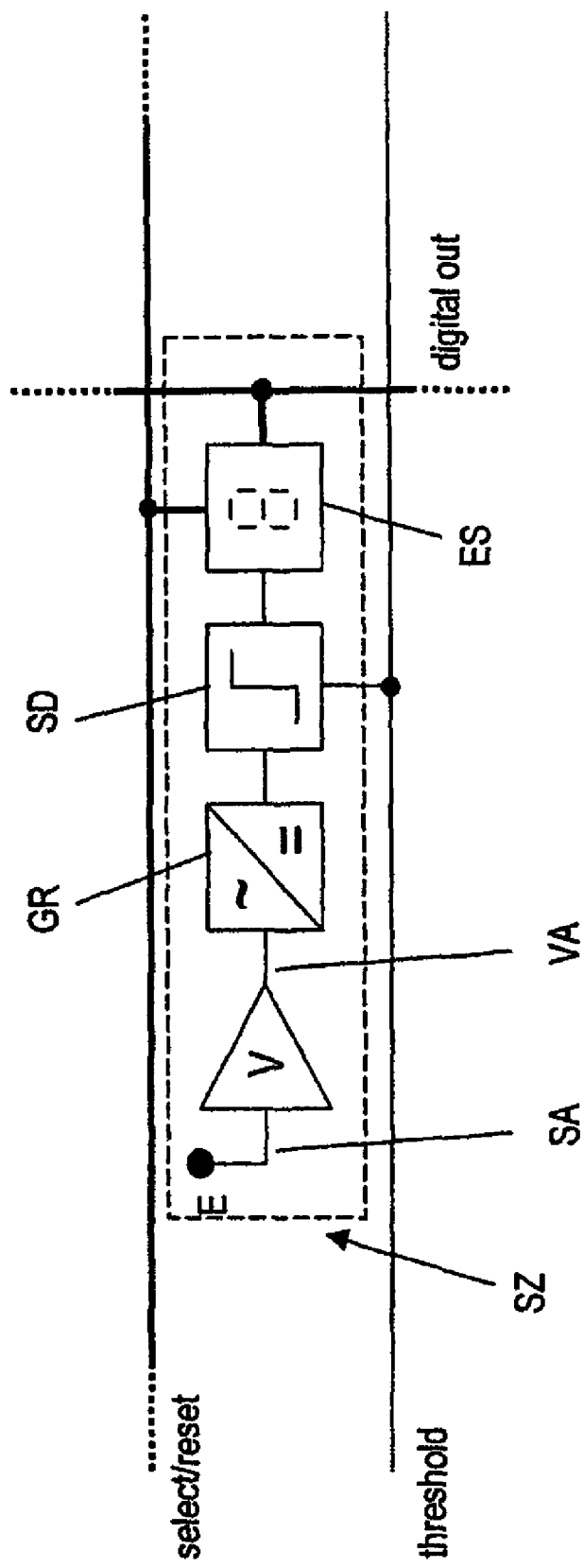
FIG. 1 shows a schematic block diagram of a sensor cell in line with a first embodiment of the invention.

FIG. 1 shows a schematic block diagram of a preferred sensor cell SZ in line with a first embodiment of the inventive apparatus. The sensor cell SZ is part of a monolithically integrated semiconductor structure, particularly a silicon CMOS structure. A multiplicity of sensor cells SZ arranged, preferably orthogonally, in the form of rows and columns form a sensor cell array which, in terms of its matrix-like design, has similarities with a memory cell array in a DRAM.

The sensor cell SZ has a sensor element which contains an electrically conductive detection electrode E for interacting with or detecting neural signals from the neural network (not shown). Optionally, the detection electrode may also be used to output electrical stimulation signals to the neural network. The signal pickup or sensor element used for the neural signal may be various sensors or transducers which are able to detect the electrical activity of neurons—"action potentials". In the simplest case, the detection electrode E of the sensor element is an "open" metal electrode, for example a gold electrode, which is arranged on the surface of the textured semiconductor substrate. The detection electrode E can come into contact with the solution or electrolyte (the neural network), so that there is electrical coupling with the neurons. However, the detection electrode E may also be an electrically conductive electrode which is coated with a dielectric.

Preferably, the detection electrode E has an electrode area which is essentially the same size as or smaller than the typical bearing area of a neuron on the sensor surface. When rat neurons are used, this gives a preferred electrode diameter of approximately 10 µm, for example. The "firing" of a neuron is manifested particularly in a temporary conductivity increase for potassium and sodium currents between the cell interior and the cell exterior. This results in an abrupt change in the electrical potential in the gap between the detection electrode E and the supported arrangement of neural cells. This arrangement can range from an individual neural cell (single unit) through accumulations of a plurality of neural cells to highly dense layers of neural tissue (multiunit). The frequency spectrum for such signals typically has a bandwidth of up to 5 kHz, the amplitude of the neural signal which can be detected on the detection electrode E being in the order of magnitude of 1 mV.

The amplifier V connected to a sensor output SA on the sensor element amplifies this signal typically by several orders of magnitude and outputs it as amplifier output signal for further signal processing via an amplifier output VA. During "firing" of a neuron, both negative and positive voltage pulses can be detected extracellularly. Since the polarity of the pulse contains no information which is necessary for assessing the activity of a neural network, it is advantageous to rectify the amplifier output signal first. To this end, a rectification element GR is provided whose rectifier input is electrically connected to the amplifier output VA.

In order to record the activity of the neural network as completely as possible, a high density of detection electrodes is advantageous, which results in the individual sensor cells needing to have small dimensions. This requires the use of components with comparatively small areas (particularly transistors with small areas) in the sensor cell SZ, which results in a comparatively high noise level (1/f noise) in the amplifier V. In order to extract a neural event from the noise, the rectification by the rectification element GR is followed by a threshold value detector element SD whose threshold value can preferably be prescribed externally. To this end, a row line "threshold" may be provided, in particular, which connects the threshold value detector element SD to a control device (not shown), which may be part of an activity evaluation device. In abstracted form, the threshold value detector element may be regarded as an analog/digital converter with a word length of one bit at the output.

When the threshold value detector element SD detects a neural event, i.e. the rectified amplifier output signal is above a predetermined threshold value, the threshold value detector output signal actuates a digital counter, for example, whose counter reading is increased by one by the received signal. The digital counter thus represents an event memory ES for storing neural events. A plurality of "select" and "reset" lines may be used to apply the counter reading from the event memory ES to digital output lines (e.g. column line "digital out"). A memory reading device (not shown) in the activity evaluation device can read the counter reading from the event memory ES in each sensor cell SZ in this manner. When reading has taken place, the event memory ES can be reset using a "reset" line. In the simplest case, the event memory ES is a latch which stores whether (at least) one neural event has taken place between two reading intervals.

The counter readings which have been read from the cells are registered and processed further at the edge of the sensor cell array. In this context, the reading process takes place in a similar manner to that in the case of DRAMs by virtue of the sensor cells SZ being addressed using selection and signal lines (word line/bit line), which permits successive digital reading at regular intervals of time. The activity of the neural network is obtained from the number of events per unit time which are stored in the event memories ES in the sensor cells SZ.

Hence, measuring the activity of the neural network requires no transfer of neural voltage transients, i.e. voltage/time profiles for the neural signals. Instead, "event characterization" takes place directly in each sensor cell SZ, so that a digital data item needs to be transferred just for each detected neural event.

Another advantage of this embodiment is that the event information can actually be read from the sensor cells SZ, and is available for further processing, in digital form. However, this requires comparatively complex circuitry for the sensor cells SZ, which means that the area of the sensor cells SZ is comparatively large and the cell density of the sensor cell array is thus comparatively small. The result of this is that only a fraction of the neurons which are statistically distributed on the sensor cell array and are sometimes free to move can be recorded by measurement.

Figure 2:
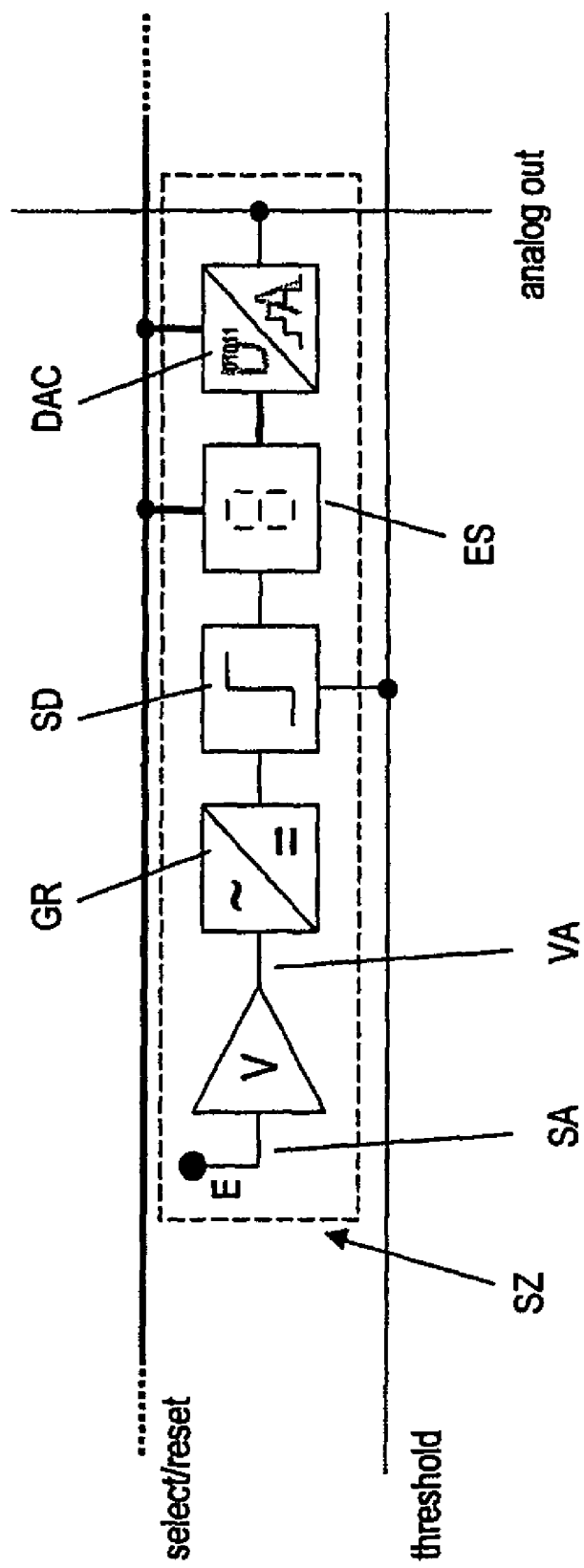
FIG. 2 shows a schematic block diagram of a sensor cell in line with a second embodiment of the invention.

FIG. 2 shows a second embodiment, which is derived from FIG. 1. Identical or similar components have the same reference symbols and are not described again. In the second embodiment, the reading on the counter (on the event memory ES) is not output directly in digital form, but rather is converted by means of a digital/analog converter DAC into an analog signal, i.e. into an analog voltage or current signal. The analog signal is applied to the column line "analog out" in the sensor cell array for the purpose of output to the activity evaluation device. The reference symbol "analog out" subsequently also denotes the corresponding evaluation input on the activity evaluation device.

An advantage in this context is that a plurality and preferably all of the sensor cells in a sensor cell array can be read simultaneously. If the output signal from the DAC is a current, then the output currents from all of the connected sensor cells are added on the column lines ("analog out"). At the edge of the sensor cell array, it is thus directly possible to measure the sum of the counter or event memory contents of the corresponding sensor cell array column as an analog signal. In addition, all of the column lines ("analog out") may also be connected together to form a single evaluation line, so that the counter readings or memory contents of all of the event memories ES in the matrix-like sensor cell array can be added in analog form and are available as the result for further processing at the edge of the matrix. In the simplest case, the event memory ES is a latch which stores whether (at least) one event has taken place in the reading interval, and the DAC is a reference current source which delivers two different reference currents $I_{event}$, $I_{no\_event}$ on the basis of the content of the latch.

Preferably, one of the two reference currents $I_{event}$ and $I_{no event}$ is equal to zero. At the edge of the matrix or of the sensor cell array, the summed current $I_{sum}=\Sigma_i \Sigma I_{ij}$ can thus be detected directly. The amplitude of this current which varies over time is a direct measure of the activity of a neural network and thus actually represents an activity signal which is preferably also amplified and/or reshaped for further processing and output via the evaluation output of the activity evaluation device.

Figures 3A, 3B:
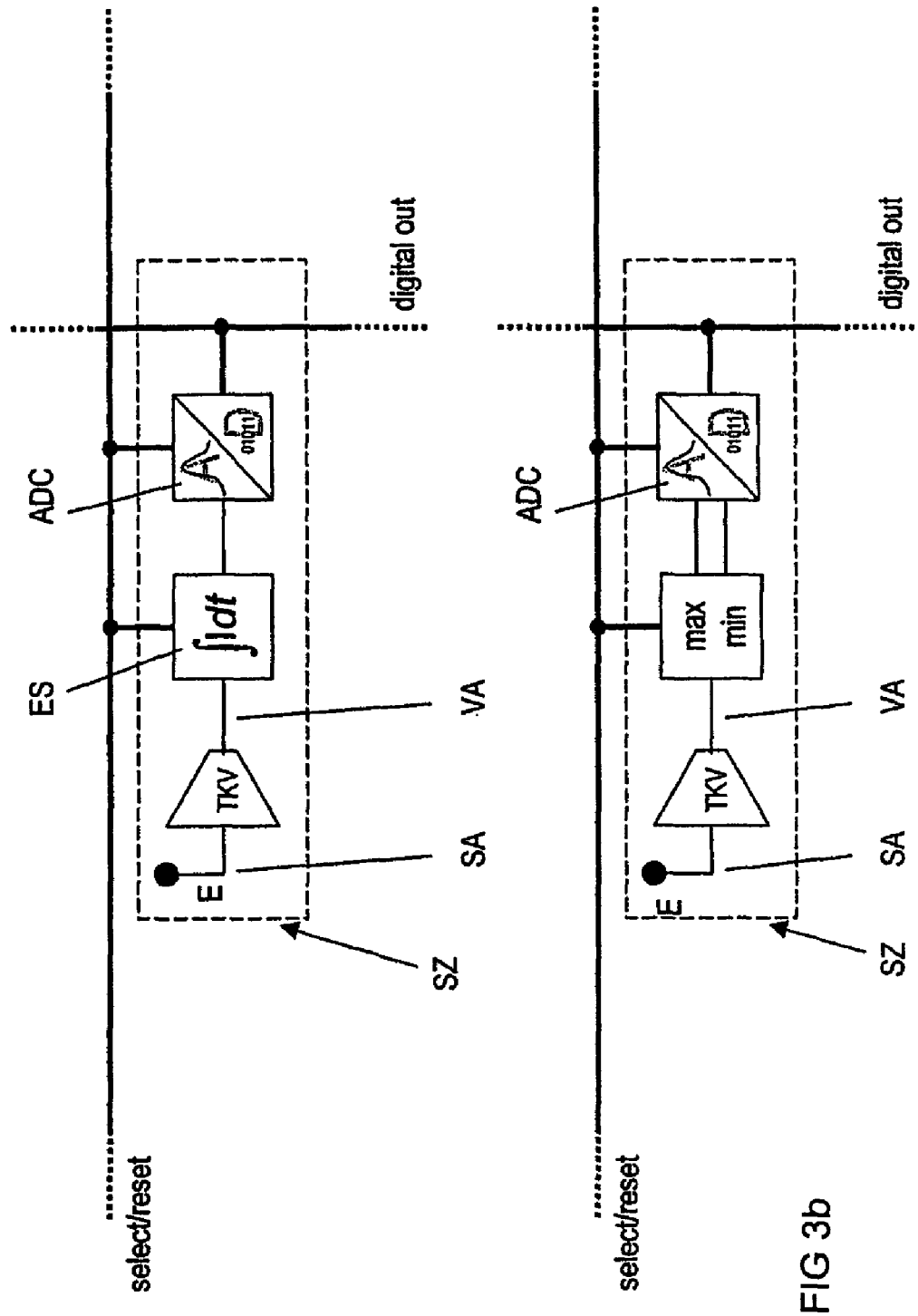
FIGS. 3*a* and 3*b* show schematic block diagrams of third embodiments of the invention.

FIGS. 3a and 3b show a third embodiment of a sensor cell SZ with associated reading and control lines and also a modification thereof, where the information from a neural event is stored in analog form in an analog event memory ES and is output in digital form. In the embodiment shown in FIG. 3a, the sensor output signal amplified in a transconductance amplifier TKV is stored in an analog integrator which forms the analog event memory ES.

In the form shown here without a rectification element, the noise is filtered by the integrator. By contrast, a neural signal changes the content of the integrator greatly, since it is typically a positive or negative pulse. In the case of a fully symmetrical neural signal, on the other hand, the integrator would store nothing. In this case, a rectification element is preferably used, which means that such neural signals are also detected, but in this case the noise signal which is likewise rectified results in an unwanted offset in the analog event memory ES. The content of the event memory may be read as a digital value from the sensor cell SZ using an analog/digital converter ADC. Row lines ("select/reset") can be used to initiate the reading of the memory content of the event memory ES and to reset the event memory ES.

In the embodiment shown in FIG. 3b, instead of an analog integrator as event memory ES there is a circuit for storing the maximum value and minimum value of an amplifier output signal. This circuit stores the maximum and minimum values of the amplifier output signal from the amplifier TKV, which appear within a reading cycle, in analog form. The connected analog/digital converter ADC converts the thus stored peak-to-peak value of the sensor signal into a digital information item and makes it available on the output line ("digital out"). When reading has taken place, the analog memory ES is reset. In one simple form, it is also possible to use just one maximum or minimum value memory. The analog/digital converter ADC may also be in the form of a simple threshold value detector.

Figure 4C:
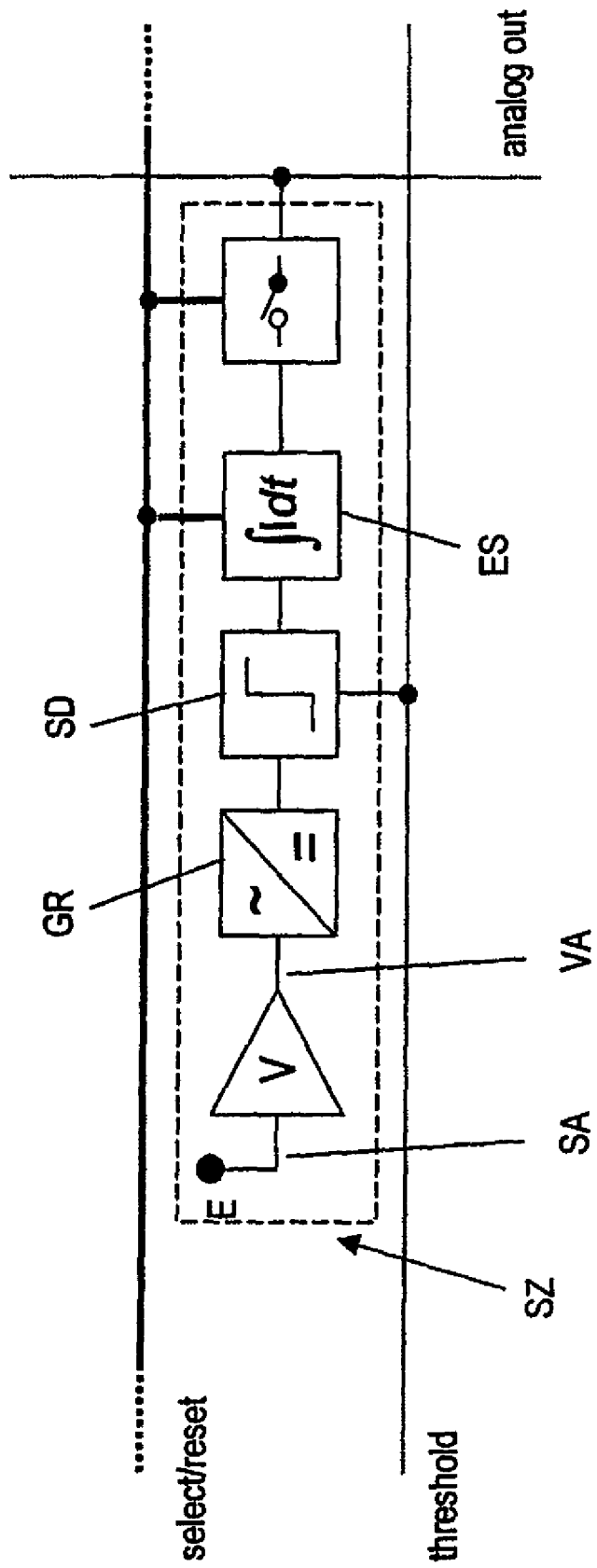

FIGS. 4a, 4b, and 4c show fourth embodiments, in which the event information is stored and output in analog form. The embodiments in FIGS. 4a and 4b are derived directly from the embodiments in FIGS. 3a and 3b. The stored analog value from the integrator or extreme value memory ES is in this case connected directly to an analog output line ("analog out") when the sensor cell SZ is read. In this case too, an output signal in the form of a current is advantageous, since in this case a plurality of sensor cells SZ on a column line can be read simultaneously.

In the embodiment in FIG. 4c, the amplified and rectified signal is first routed through a threshold value detector element SD before the information whose values have been discretized in this manner is stored in an integrator ES. This means that the influence of the noise on the event memory content of the event memory ES which is in the form of an integrator can largely be suppressed.

Figure 5:
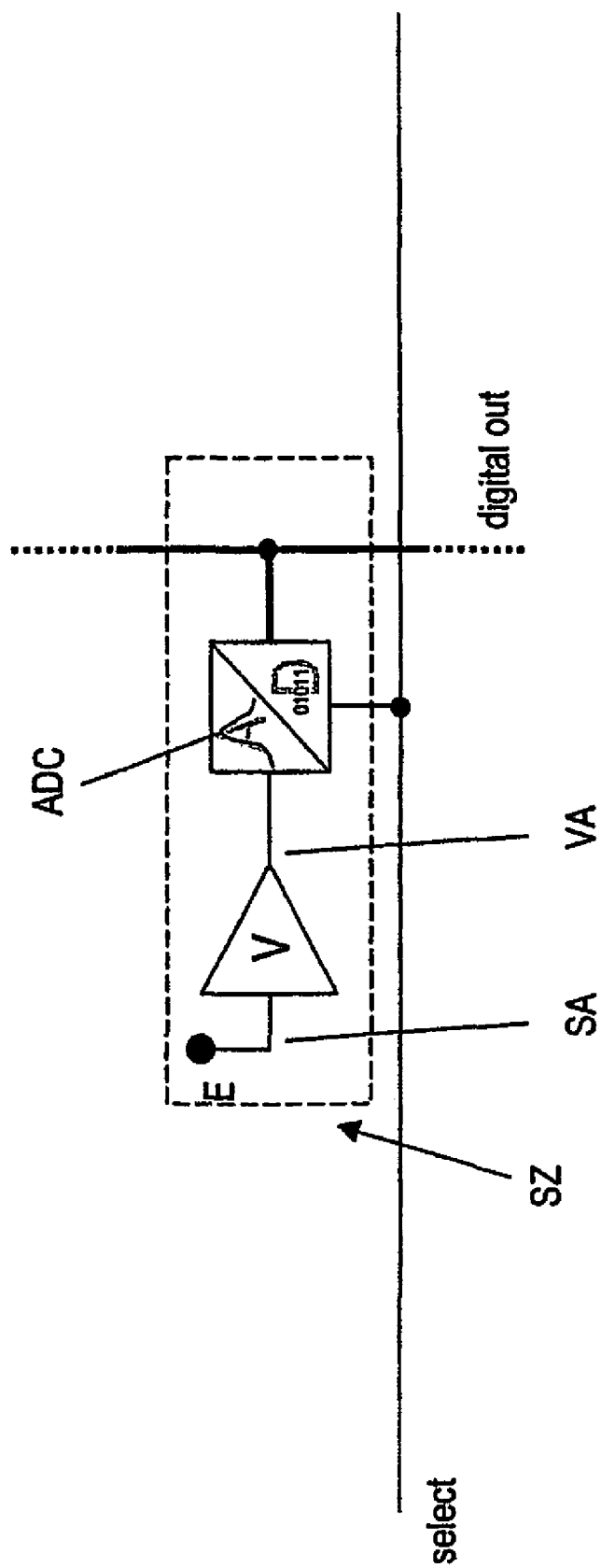
FIG. 5 shows a schematic block diagram of a fifth embodiment of the invention.

FIG. 5 shows a fifth embodiment, in which the event is not stored in the sensor cell SZ. The amplifier output signal is connected directly to an ADC which, following activation by the "select" line, outputs its measured value to the digital output or evaluation line.

Figure 6A:
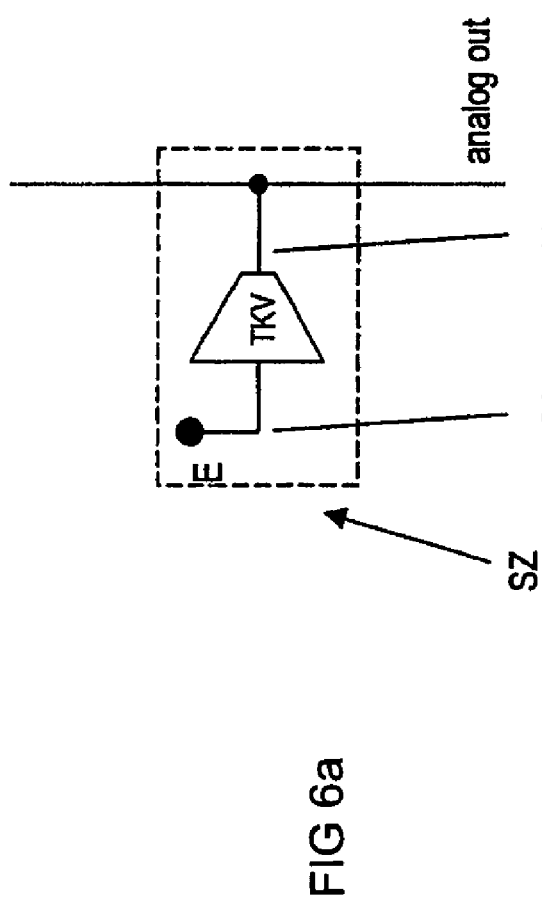
FIGS. 6*a* and 6*b* show schematic block diagrams of sixth embodiments of the invention.
Figure 6B:
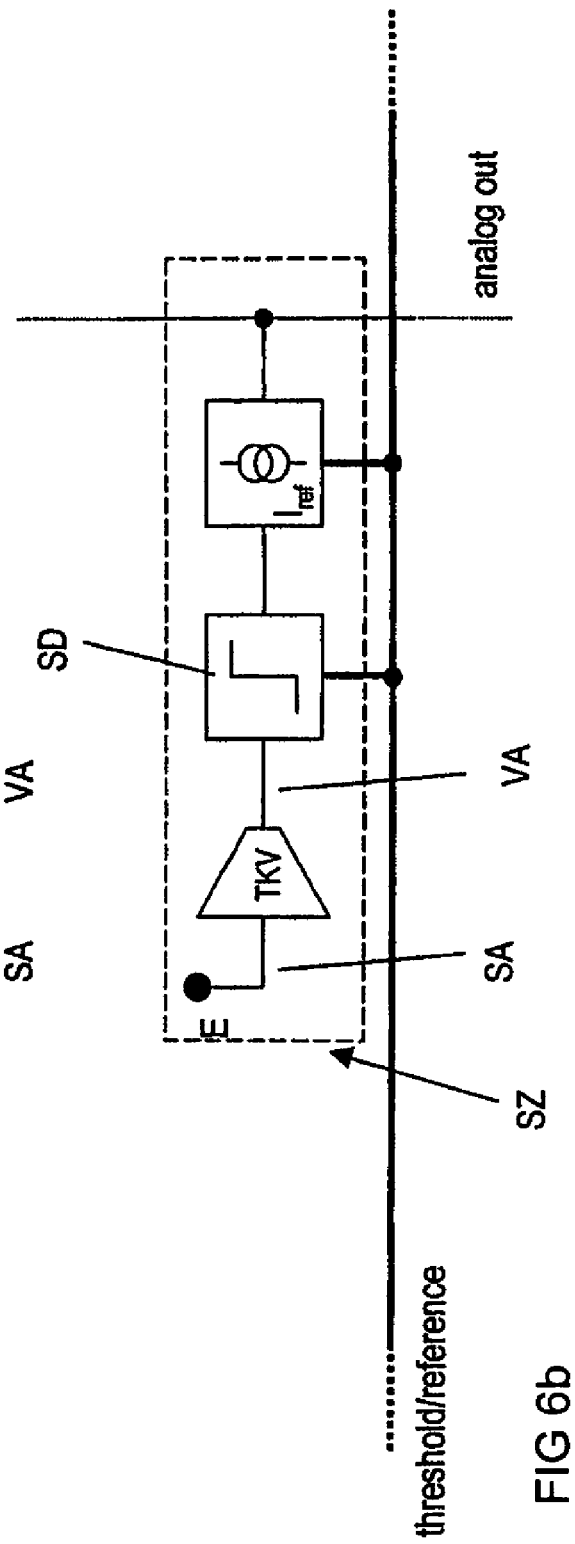

FIGS. 6a and 6b show sixth embodiments, in which neither neural events are stored nor sensor cells SZ to be read are selected. In the embodiment shown in FIG. 6a, the current output of a transconductance amplifier TKV is connected directly to the corresponding column line serving as evaluation line. The current output signal from the amplifier TKV is added on the column line ("analog out") to the current output signals from all other connected sensor cells. At the edge of the sensor cell array, it is thus possible to tap off the summed current signal, which is all of the individual signals or amplifier output signals from the sensor cells overlaid.

The noise power from the n sensor cells connected to the column line adds up, so that the current noise for the entire column is obtained on the basis of $I_{noise, column}=$ $I_{noise,Column}=\sqrt{n}I_{noise,Cell}$. By contrast, the neural signals from an active network are heavily correlated, which means that the signal or evaluation current on the column line in the extreme case (full overlaying of the signals) assumes the value $I_{signal,column}=nI_{signal,cell}$.

In the embodiment shown in FIG. 6b, the transconductance amplifier TKV has a threshold value detector element SD connected downstream whose threshold value can preferably be set externally using a "threshold" line. The threshold value detector element SD makes it possible to discriminate between the noise signal and a neural event, provided that the signal-to-noise ratio is sufficient and the threshold value is set appropriately. The output signal from the threshold value detector element actuates a reference current source IREF which is connected to the output or evaluation line ("analog out"). In quite general terms, it is possible for any circuit block which serves to improve the signal-to-noise ratio or to isolate the useful signal from the noise signal to be provided between the amplifier output VA and the output line "analog out".

Figure 8:
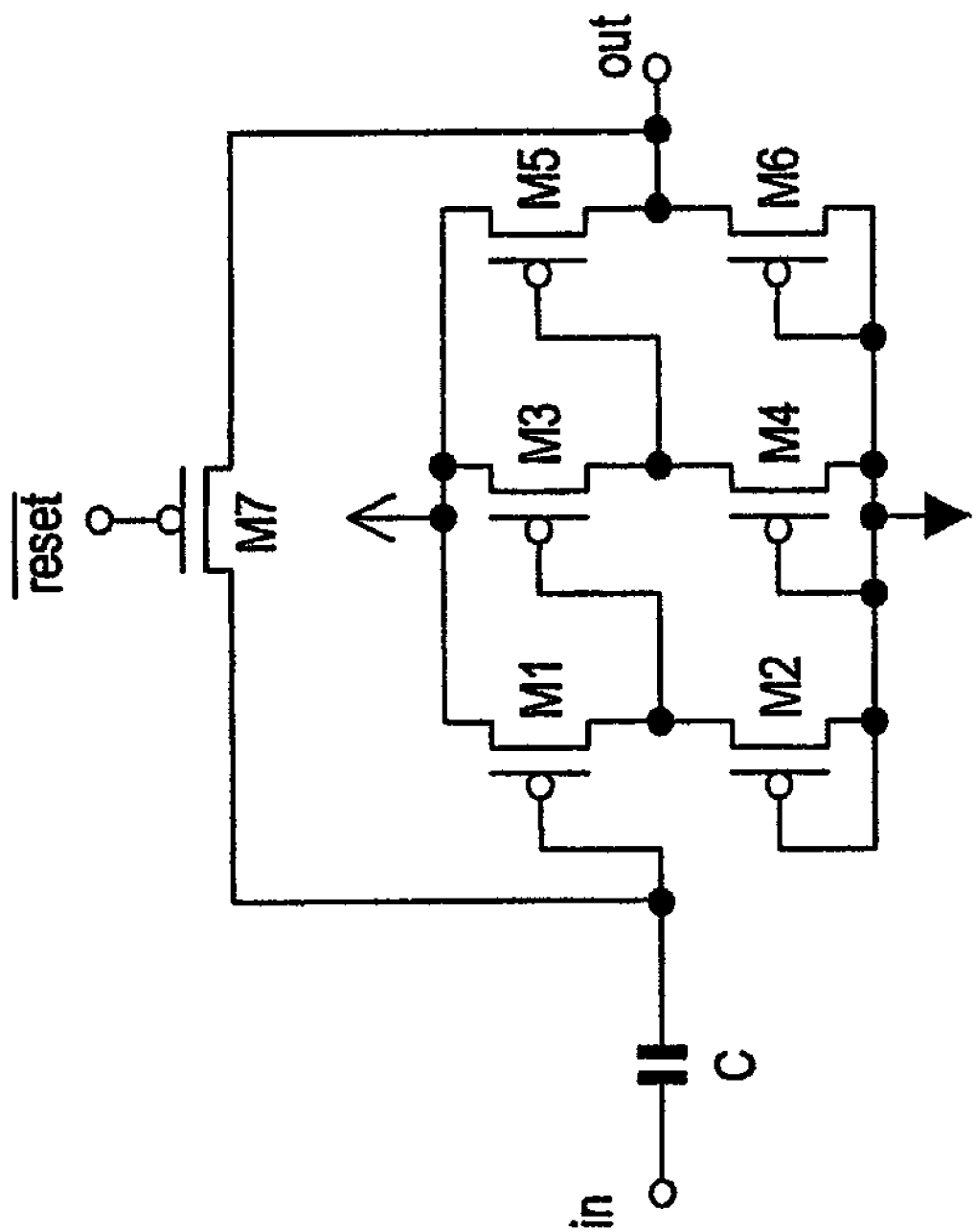
FIG. 8 shows an embodiment of a preferred inventive amplifier element with PMOS transistors.

FIG. 8 shows a voltage amplifier which is made exclusively of PMOS transistors. This is advantageous particularly with respect to the greatest possible degree of miniaturization for the sensor cells SZ, since the simultaneous use of NMOS and PMOS transistors in a cell results in an increased area requirement on account of the well implantation which is then necessary. The amplifier circuit shown here comprises three stages, each of the stages having a fixed voltage gain which has been set using the (width/length) W/L ratios of the transistors. If, by way of example, the transistor M1 has a W/L ratio of 10:1 and transistor M2 has a W/L ratio of 1:10, then the gain of the first stage is approximately 10. If the other two substages of the amplifier also have this W/L ratio, then a gain factor of approximately 1000 is obtained for the whole circuit. The switching transistor M7 in connection with the capacitor C is used for setting the operating point of the amplifier. When the transistor M7 is on, a voltage becomes established at the input node of the amplifier (between C and gate of M1) and ensures that the amplifier at the output is not overdriven and hits the operating voltage limits. During operation, M7 is turned off, which means that the voltage stored on the capacitive input node in the calibration cycle is maintained and the amplifier is thus operated at the optimum operating point.

Figure 9A:
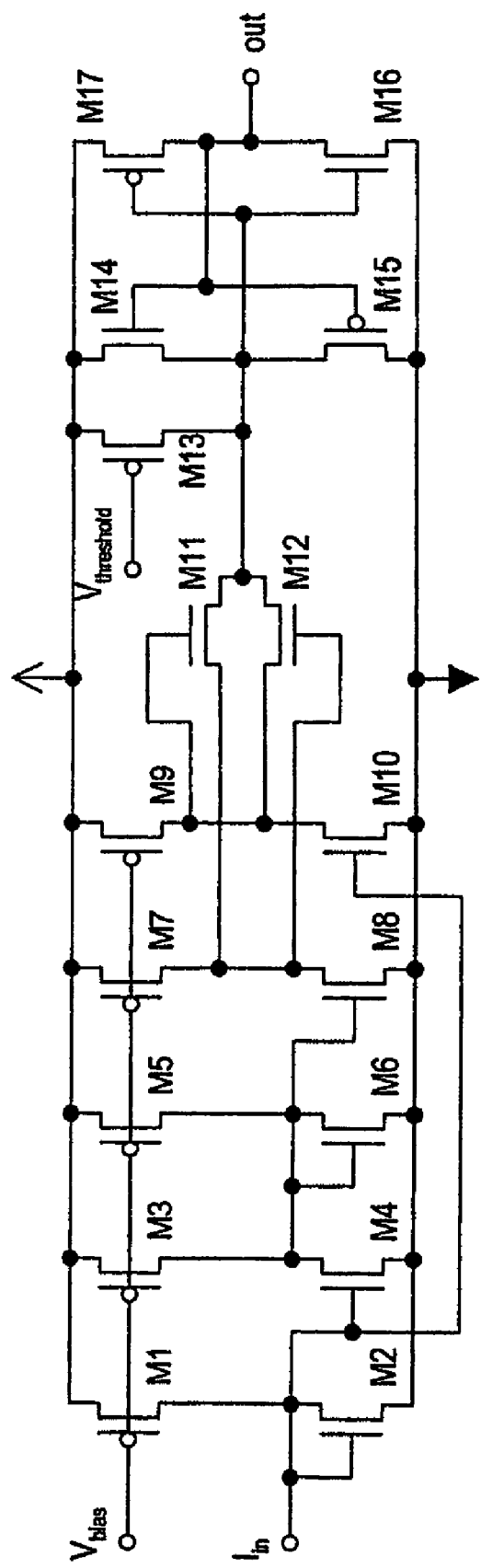
FIG. 9*a* shows a preferred embodiment of a rectification element and of a threshold value detector element.
Figure 9B:
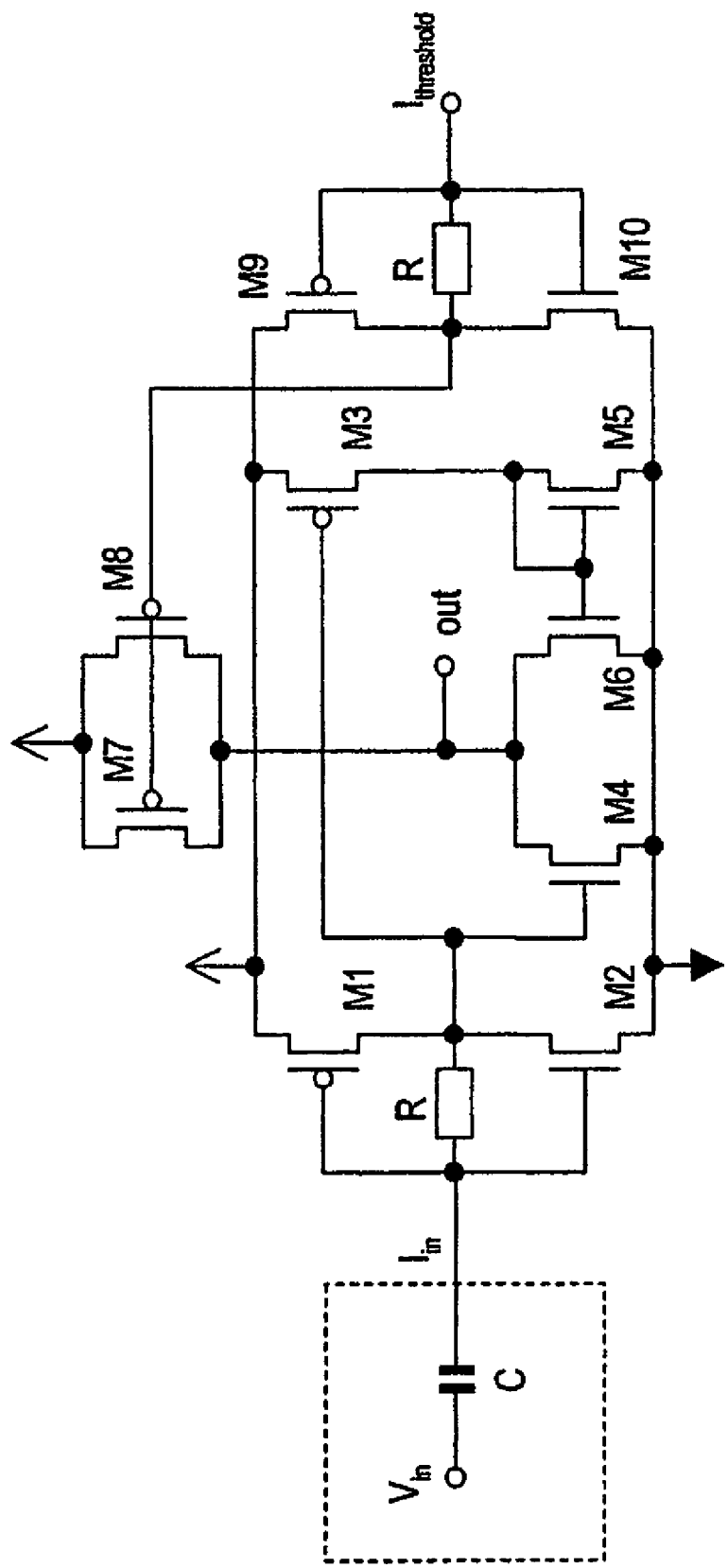
FIG. 9b shows a further preferred embodiment of a preferred rectification element and of a threshold value detector element.

FIGS. 9a and 9b show preferred embodiments of rectification elements and threshold value detector elements for current signals.

In FIG. 9a, current mirrors are used to produce a copy and an inverted copy of the current input signal (M1-M10). The signals conditioned in this manner are alternately passed by the transistors M11 and M12 according to polarity and are evaluated by the connected threshold value detector. M13 acts as a constant current source for the threshold value, while the circuit comprising M14-M17 operates as a zero current detector.

In FIG. 9b, the nonlinear characteristic curve for the MOS transistors is utilized in order to attain a rectification effect. The feedback input inverter (M1 and M2) serves as a current sink for the input current and converts it into a voltage. The value of the resistor R can be used to set the transconductance of the input stage. For an input current of $I_{in}=0$, the operating point of the circuit is set such that the same current flows through M1 and M2. Preferably, M1 and M3 and also M2 and M4 each have the same electrical properties, that is to say the same length and width of the channel. If an alternating current is applied to the input of the circuit, it is rectified nonlinearly by the transistors M3-M6.

The reference circuit comprising transistors M7-M10 provides a comparison current for the summed current from M4 and M6, so that the comparison result is actually available in digital form at the output of the circuit (out). If the current input of the two circuits has a capacitor connected upstream of it in series, then the circuits are also suitable for voltage input signals. A changing voltage signal gives rise to a displacement current in the capacitor which can be processed by the proposed circuit.

Figure 10A:
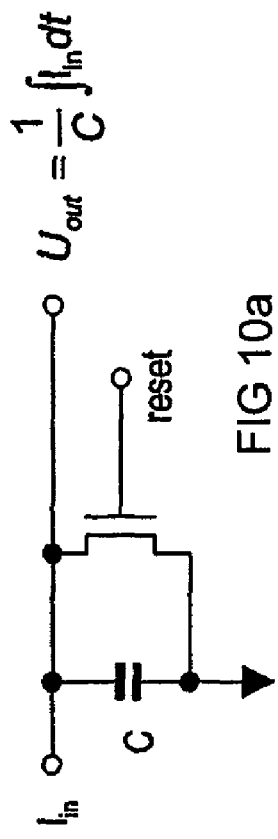
FIGS. 10a, 10b, and 10c show preferred embodiments of an analog integrator and of an analog extreme value memory.
Figure 10C:
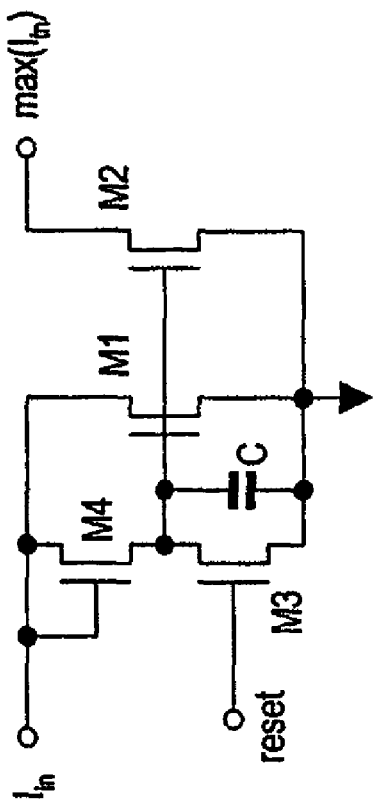
Figure 10B:
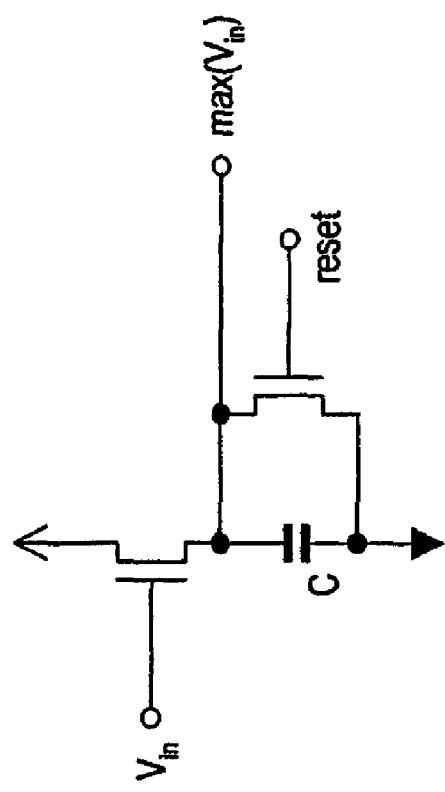

FIGS. 10a, 10b, and 10c show preferred embodiments of analog event memories ES. The embodiment shown in FIG. 10a represents a simple analog integrator with reset capability. The charge carriers in the input current $I_{in}$ are stored in the capacitor C, so that an output voltage of $$U_{out} = \frac{1}{C}\int I_{in}\,dt$$

becomes established. When the memory content has been measured or read, the memory can be emptied again by triggering the reset transistor.

The two circuits shown in FIGS. 10b and 10c are designed for analog storage of a maximum input voltage (on the left) and a maximum input current (on the right). For the memory circuit for the maximum input voltage (on the left), the memory element used is a capacitor. The capacitor follows the input voltage using a source follower circuit with an offset which is obtained essentially from the threshold voltage of the transistor. When the memory content has been measured or read, the memory can be emptied again by triggering the reset transistor.

In the memory circuit for the maximum input current, the transistor M4 operates as a diode via which the gate voltage on the current-determining transistor M1 is increased until the input current is compensated for. When the input current falls again, the gate voltage on M1 remains almost at the value which was reached previously. The stored maximum value of the input current can be taken from the drain connection of the transistor M2, which forms a current mirror together with transistor M1.

If the maximum value memories presented here are of complementary design, then minimum value memories are obtained, that is to say a memory for the maximum negative current.

Figure 11:
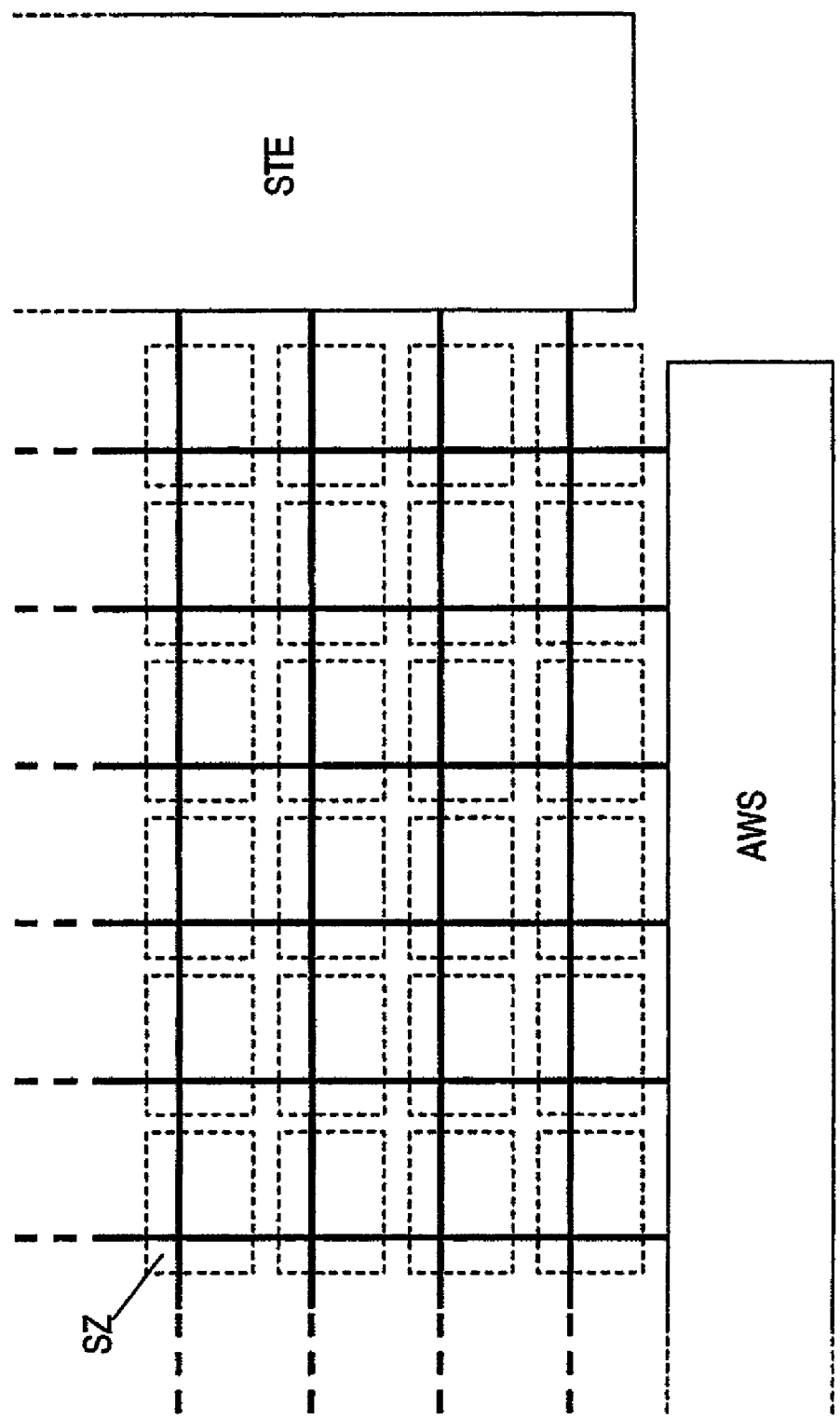
FIG. 11 shows a preferred arrangement of a sensor cell array in matrix form, with each sensor cell being able to be actuated and read by various row and column lines which span the entire arrangement.

FIG. 11 shows a preferred matrix-like arrangement of the sensor cells to form a sensor cell array, the current, supply and reading lines and also the evaluation, control and operating circuits at the edge of the sensor cell array (matrix). The orthogonal arrangement of the cells and lines (orthogonal row and column lines) is the preferred embodiment, but diagonal lines and, by way of example, a hexagonal arrangement of the sensor cells are also possible. In FIG. 11, the reference symbol STE denotes a control device for control signals and auxiliary voltages, and the reference symbol AWS denotes a digital/analog evaluation circuit. The control device STE and the evaluation circuit AWS are part of the activity evaluation device.

Figure 12:
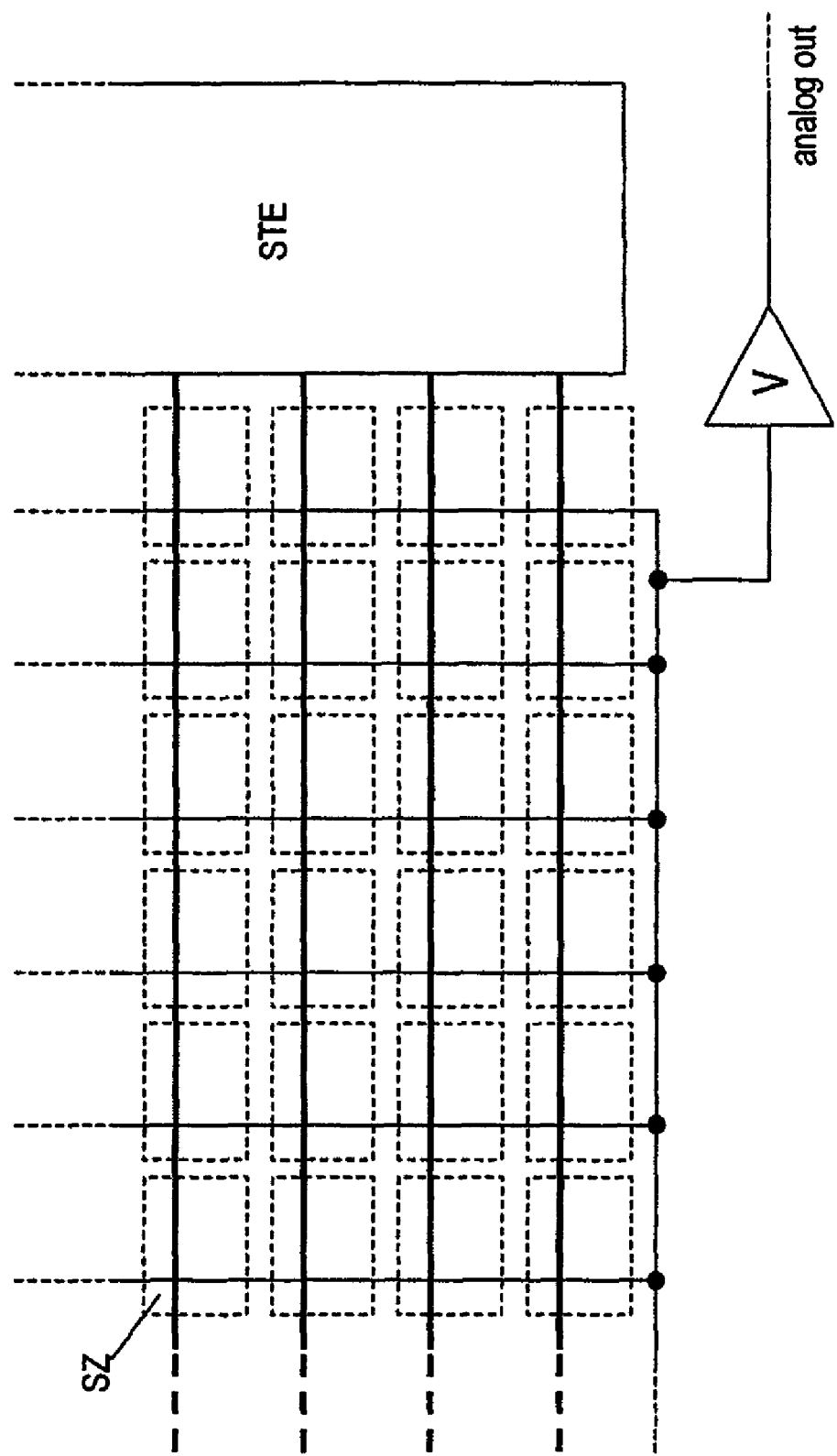
FIG. 12 shows a schematic block diagram of a preferred sensor cell array, with the collecting lines for the analog current output signals being combined at the edge of the sensor cell array and amplified.

FIG. 12 shows a preferred embodiment of a sensor cell array with a control device STE when the neural signals are subjected to purely analog signal processing, as described in connection with the 6th embodiment. The analog output or evaluation lines (column lines) are combined at the edge of the sensor cell array and are conditioned for further processing using a suitable amplifier V with a current input.

Figure 13:
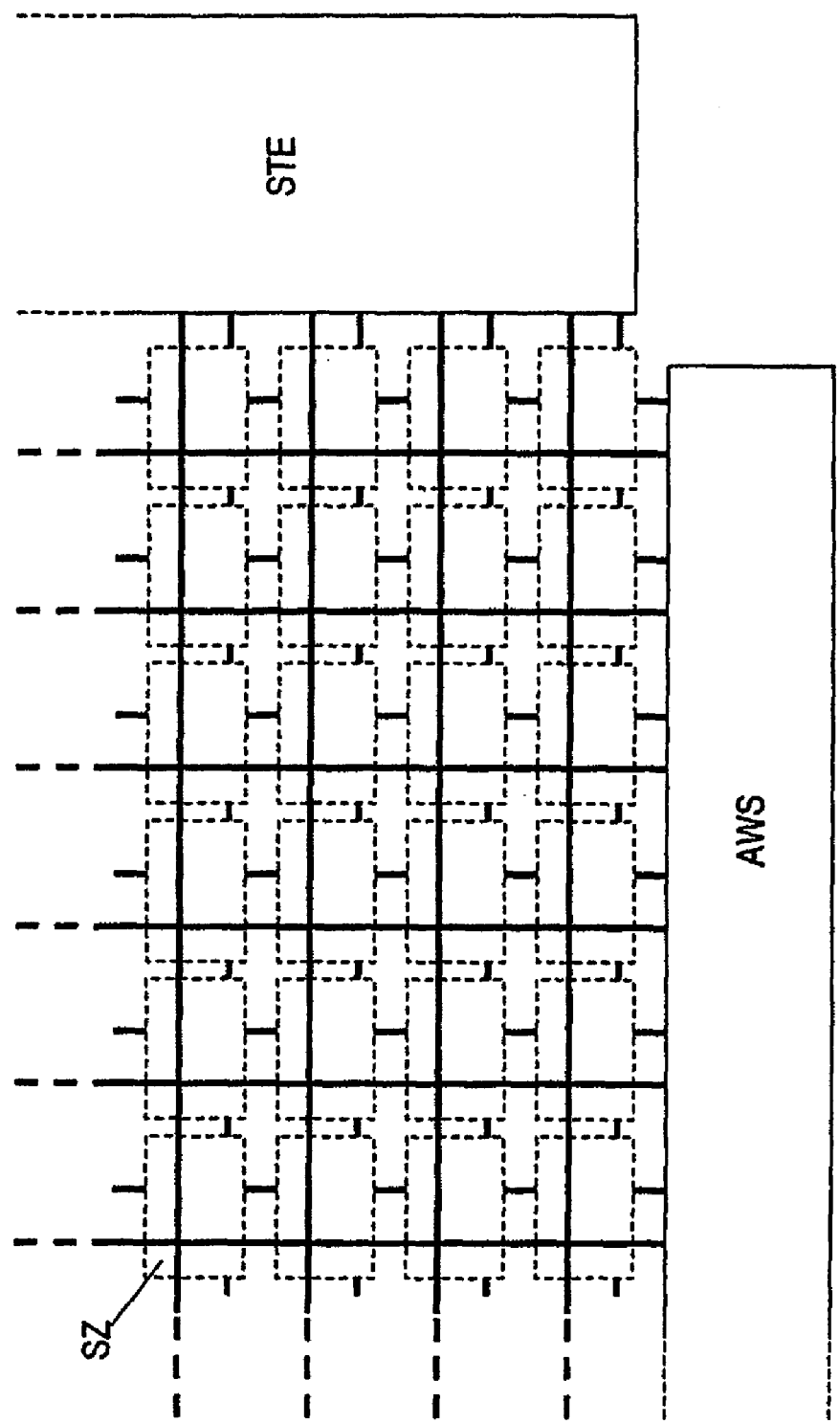
FIG. 13 shows a further preferred embodiment of a sensor cell array in matrix form, with each cell being able to be actuated and read by various row and column lines which span the entire arrangement, and additionally data of any type being able to be interchanged between the sensor cells.

FIG. 13 shows a preferred embodiment of a sensor cell array with a control device STE and an evaluation circuit AWS, in which the sensor cells SZ are able to interchange information directly with one another as well. Preferably, cells in the immediate vicinity interchange information of analog or digital type about neural events in order to permit further improvement of the detection sensitivity and/or further miniaturization of the sensor cells SZ and/or preprocessing of the recorded information. In this case, the interchanged information may be any analog or digital signal which has been described in the previously described embodiments of the sensor cells SZ.

Particularly in the case of the first embodiment (digital storage/digital output), a shift register can be provided within the sensor cells SZ, so that the stored information in the cells can be read successively from a column or row. This has the particular advantage that the digital data does not need to be read from the sensor cell SZ via a line which spans the whole column or row and has a high parasitic capacitance, but rather need only be forwarded locally from one sensor cell SZ to the next. After a plurality of clock cycles, all data are thus available at the edge of the sensor cell array for further processing.

For all of the embodiments described above, each sensor cell SZ may preferably be designed in order to be activated or deactivated via a control line. In this connection, deactivated means particularly that any neural events taking place do not give rise to a signal at the output of the sensor cell and, particularly in the case of analog transfer of the sensor information, no noise signal is then fed into the output or evaluation line either.

The invention claimed is:

1. An apparatus for measuring the activity of neural networks with a textured semiconductor substrate, comprising:
   a plurality of sensor elements with at least one respective electrically conductive detection electrode which is arranged on the surface of the semiconductor substrate to detect neural signals from a neural network, the sensor elements being designed such that the detected neural signals are a basis for outputting electrical sensor output signals via respective sensor outputs on the sensor elements;
   a plurality of amplifier elements with at least one respective amplifier input and at least one respective amplifier output, each of the sensor elements having associated one of the amplifier elements whose amplifier input is electrically connected to the sensor output of the respective sensor element, and the amplified sensor output signal being output as an amplifier output signal via the amplifier output; and
   at least one activity evaluation device with a plurality of event memories configured to store neural events, at least one memory reading device configured to read the event memories, at least one evaluation input, and at least one evaluation output, the evaluation input being electrically connected to at least one of the amplifier outputs, and the activity evaluation device being designed to produce an activity signal, which is a measure of the activity of the neural network based on of the amplifier output signal and to output the amplifier output signal via the evaluation output,
   wherein the plurality of sensor elements do not transfer transient data to the activity evaluation device.

2. The apparatus as claimed in claim 1, further comprising a plurality of sensor cells which respectively comprise one of the sensor elements with its associated amplifier element, and which are arranged in matrix form to form a sensor cell array.

3. The apparatus as claimed in claim 2, wherein each of the sensor cells comprises one of the event memories, whose event memory input is connected to the amplifier output.

4. The apparatus as claimed in claim 3, wherein each of the event memories is selected via a select line in the activity evaluation device for selective reading by the memory reading device.

5. The apparatus as claimed in claim 1, wherein the activity evaluation device is designed for reading the event memories during predetermined time periods and for producing the activity signal based on the memory contents read from the event memories per time period.

6. The apparatus as claimed in claim 1, wherein the amplifier elements are connected to the associated event memories via respective threshold value detector elements for discretizing the amplifier output signals.

7. The apparatus as claimed in claim 6, wherein the amplifier elements are connected to the associated threshold value detector elements via respective rectification elements for configured to rectify the amplifier output signal.

8. The apparatus as claimed in claim 1, wherein the event memory elements are digital counters.

9. The apparatus as claimed in claim 1, wherein the event memory elements are analog integrators or analog minimum or maximum memories.

10. The apparatus as claimed in claim 1, wherein the amplifier elements are transconductance amplifier elements for producing a current signal as the amplifier output signal.

11. The apparatus as claimed in claim 1, wherein the amplifier elements are transconductance amplifier elements for producing a current signal as the amplifier output signal, the amplifier outputs of at least two of the amplifier elements are connected to the activity evaluation device via a single evaluation line, so that the current signals from the at least two amplifier elements are added, and the activity evaluation device is designed such that the activity signal is produced based on the amplitude of the added current signal.

12. The apparatus as claimed in claim 11, wherein the amplifier outputs of all of the amplifier elements are connected to the activity evaluation device via a single evaluation line.

13. The apparatus as claimed in claim 11, wherein the amplifier elements are connected to the activity evaluation device via a single evaluation line via respective threshold value detector elements for discretizing the amplifier output signals and downstream reference current sources.

14. The apparatus as claimed in claim 1, wherein at least two of the sensor cells are connected to one another for signaling purposes such that at least one signal from the sensor cells is interchanged between the sensor cells.

15. A method for measuring the activity of neural networks using an apparatus as claimed in claim 1, comprising the steps of:
   detecting the neural signals using the plurality of sensor elements;
   producing and outputting the sensor output signals based on the detected neural signals;
   amplifying the sensor output signals using the respective amplifier elements in order to produce the amplifier output signals; and
   producing the activity signal, which is a measure of the activity of the neural network, based on the amplifier output signals and not based directly on transient data.

* * * * *